(12) United States Patent
Burkholz et al.

(10) Patent No.: US 11,406,795 B2
(45) Date of Patent: Aug. 9, 2022

(54) DELIVERY DEVICE FOR A VASCULAR ACCESS INSTRUMENT

(71) Applicant: Becton, Dickinson and Company, Franklin Lakes, NJ (US)

(72) Inventors: Jonathan Karl Burkholz, Salt Lake City, UT (US); Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 208 days.

(21) Appl. No.: 16/502,541

(22) Filed: Jul. 3, 2019

(65) Prior Publication Data

US 2020/0016374 A1 Jan. 16, 2020

Related U.S. Application Data

(60) Provisional application No. 62/696,229, filed on Jul. 10, 2018.

(51) Int. Cl.
*A61M 25/06* (2006.01)
*A61M 25/09* (2006.01)
*A61B 5/15* (2006.01)

(52) U.S. Cl.
CPC ... *A61M 25/0606* (2013.01); *A61B 5/150396* (2013.01); *A61M 25/065* (2013.01); *A61M 25/0637* (2013.01); *A61M 25/09* (2013.01); *A61B 5/150992* (2013.01); *A61M 2025/0681* (2013.01)

(58) Field of Classification Search
CPC .............. A61M 25/0637; A61M 25/09; A61M 25/065; A61M 25/09041; A61M 25/0606; A61M 25/0113; A61M 2025/0681; A61B 5/150992; A61B 17/3415; A61B 2017/3445; A61B 5/150396
See application file for complete search history.

(56) References Cited

U.S. PATENT DOCUMENTS

| 7,449,002 B1 | 11/2008 | Wenstad |
| 8,366,685 B2 * | 2/2013 | Devgon .......... A61B 5/150511 604/263 |
| 9,186,100 B2 | 11/2015 | Devgon |
| 9,744,344 B1 | 8/2017 | Devgon et al. |

(Continued)

FOREIGN PATENT DOCUMENTS

WO 2018/175529 9/2018

*Primary Examiner* — Nilay J Shah
*Assistant Examiner* — Robert F Allen
(74) *Attorney, Agent, or Firm* — Kirton McConkie; Whitney Blair; Kevin Stinger

(57) ABSTRACT

A delivery device for delivering an instrument into a catheter assembly may include a housing having a proximal end, a distal end, and a slot. The delivery device may include a guide feature, which may be disposed within the housing. The guide feature may extend through the slot. The delivery device may include an instrument disposed within the housing and extending through the guide feature. In response to movement of the guide feature along the slot in the distal direction a first distance, a first end of the instrument may be advanced in the distal direction a second distance, which may be greater than the first distance. A second end of the instrument may be stationary with respect to the housing.

15 Claims, 6 Drawing Sheets

(56) References Cited

U.S. PATENT DOCUMENTS

| | | | |
|---|---|---|---|
| 2014/0094774 A1* | 4/2014 | Blanchard | A61M 25/0097 604/506 |
| 2014/0188002 A1 | 7/2014 | Close et al. | |
| 2015/0119806 A1 | 4/2015 | Blanchard | |
| 2016/0045715 A1* | 2/2016 | Galgano | A61M 25/0662 604/510 |
| 2016/0331938 A1* | 11/2016 | Blanchard | A61M 25/0618 |
| 2017/0216564 A1* | 8/2017 | Devgon | A61M 25/0113 |
| 2017/0360345 A1 | 12/2017 | Devgon | |
| 2018/0272106 A1* | 9/2018 | Funk | A61B 5/15003 |

* cited by examiner

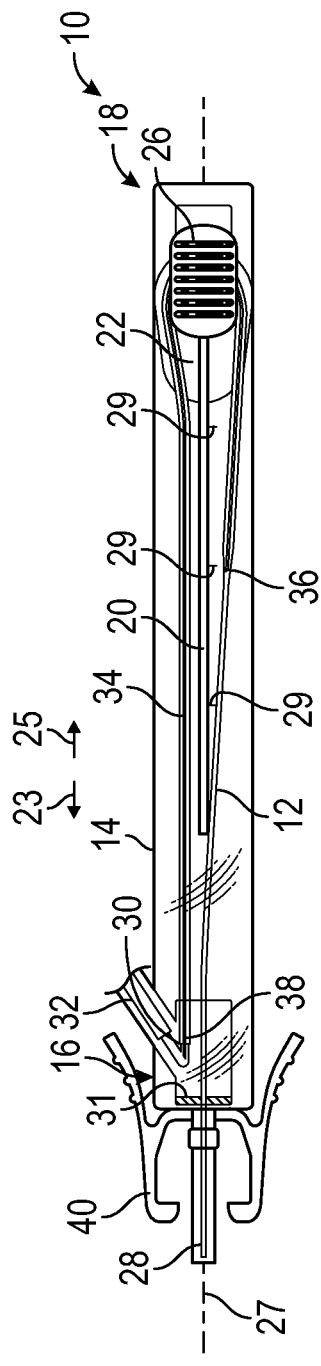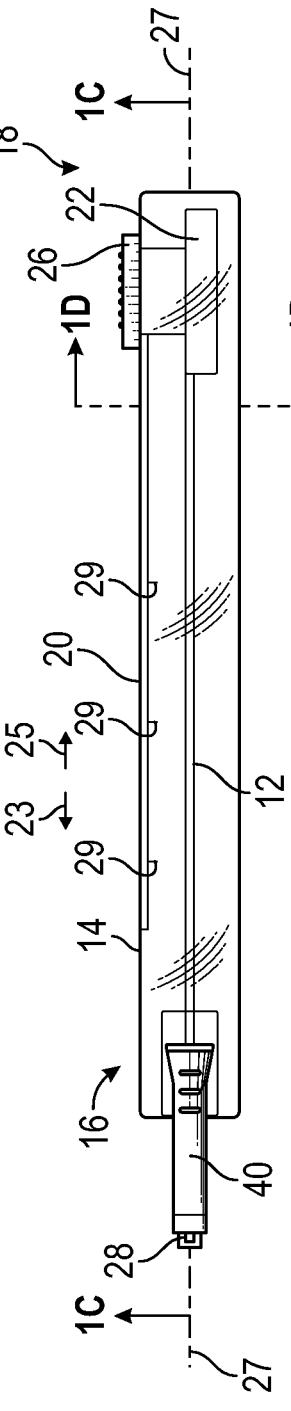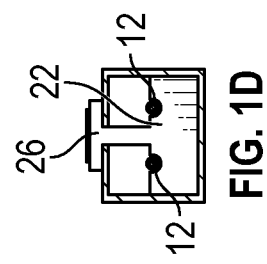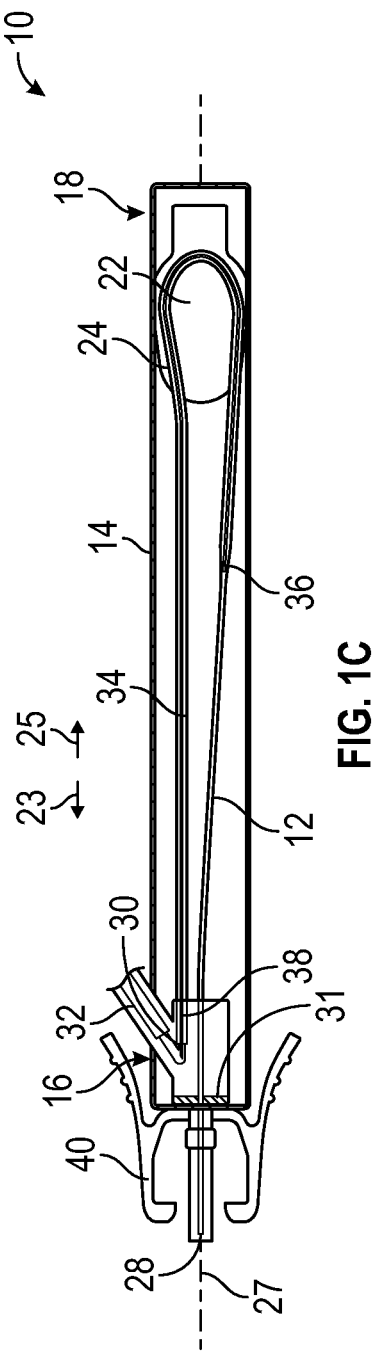

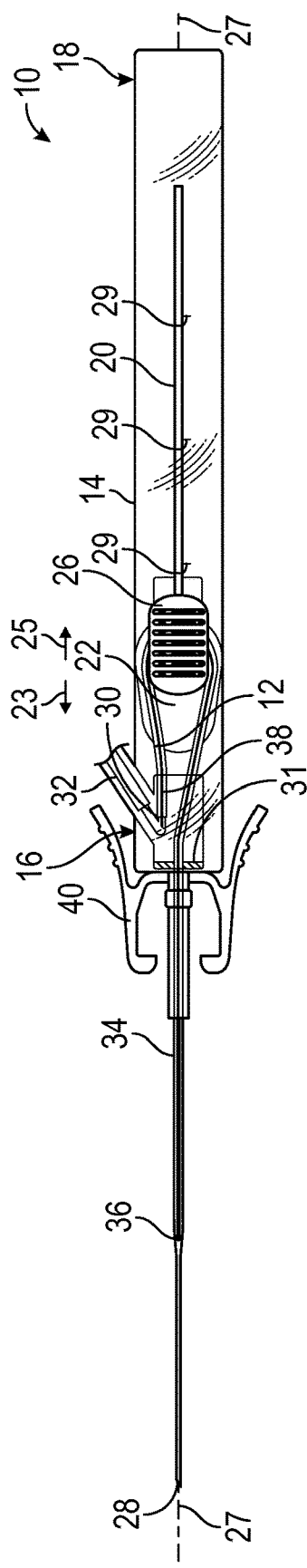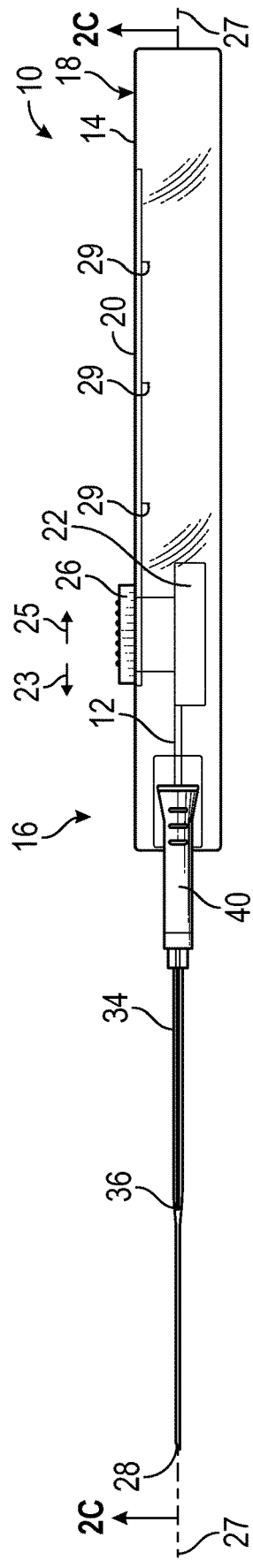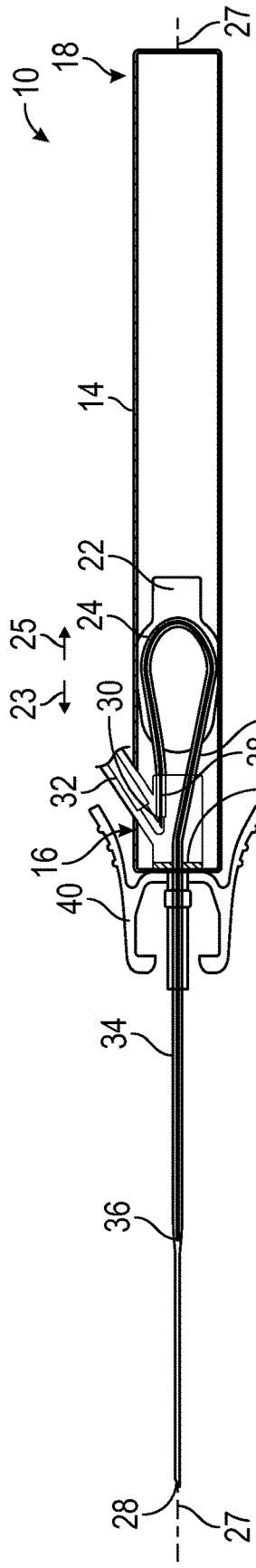

DELIVERY DEVICE FOR A VASCULAR ACCESS INSTRUMENT

RELATED APPLICATIONS

This application claims the benefit of U.S. application Ser. No. 62/696,229, filed Jul. 10, 2018, and entitled DELIVERY DEVICE FOR A VASCULAR ACCESS INSTRUMENT, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is required, an additional needle stick is needed to provide vein access for blood collection, which may be painful for the patient and result in higher material costs. Accordingly, there is a need for catheter systems and methods that facilitate placement of blood sample instruments, such as, for example, catheters, and probe instruments in the vasculature of the patient without additional needle sticks.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a delivery device for delivering a vascular access instrument into a catheter assembly and/or vein of a patient, as well as related systems and methods. In some embodiments, the delivery device may include a housing having a proximal end, a distal end, and a slot. In some embodiments, the delivery device may include a guide feature, which may be disposed within the housing. In some embodiments, the guide feature may extend through the slot. In some embodiments, the guide feature may include a channel, which may be generally U-shaped. In some embodiments, the guide feature may include an advancement tab, which may be configured to be moved by a hand of a user.

In some embodiments, the delivery device may include an instrument disposed within the housing and extending through the guide feature. For example, in some embodiments, the instrument may extend through the channel. In some embodiments, in response to movement of the guide feature along the slot in the distal direction a first distance, a first end of the instrument may be advanced in the distal direction a second distance, which may be greater than the first distance. In some embodiments, the second distance may be two times the first distance. In some embodiments, a second end of the instrument may be stationary with respect to the housing. In some embodiments, the first end of the instrument may be advanced in the distal direction beyond the distal end of the housing in response to the guide feature being partially and/or fully advanced along the slot in the distal direction.

In some embodiments, the instrument may include a probe, a light tube for disinfection, or another suitable instrument. In some embodiments, the instrument may include a catheter. In these and other embodiments, the housing may include extension tubing, which may extend outwardly from a distal portion of the housing. In some embodiments, the second end of the instrument may be coupled to the extension tubing.

In some embodiments, a guidewire may be disposed within the catheter. In some embodiments, in response to movement of the guide feature along the slot in the distal direction, the guidewire may move through the channel. In some embodiments, the first end of the guidewire may be advanced in the distal direction beyond the distal end of the housing in response to the guide feature being partially and/or fully advanced along the slot in the distal direction.

In some embodiments, the delivery device may include support tubing, which may extend from and be coupled to the guide feature. In some embodiments, in response to movement of the guide feature along the slot in the distal direction, the instrument may move through the support tubing.

In some embodiments, the channel may be horizontally or vertically oriented within the housing. In some embodiments, a portion of the instrument between the second end of the instrument and the guide feature may be generally parallel with a longitudinal axis of the delivery device. In some embodiments, the portion of the instrument between the second end of the instrument and the guide feature may be angled with respect to the longitudinal axis of the delivery device. In some embodiments, a portion of the instrument between the first end of the instrument and the guide feature may be parallel with the longitudinal axis of the delivery device. In some embodiments, the portion of the instrument between the first end of the instrument and the guide feature may be angled with respect to the longitudinal axis of the delivery device.

In some embodiments, the delivery device may allow the instrument to access vasculature of a patient through another vascular access device, such as, for example, a catheter assembly, which may be inserted into the vasculature of the patient. In some embodiments, when the instrument is introduced into the catheter assembly via delivery device, the instrument may access a fluid pathway of the catheter assembly and/or the instrument may extend through the catheter assembly and access the vasculature of the patient. In some embodiments, the catheter assembly may include a catheter adapter and another catheter, which may extend distally from the catheter adapter. In some embodiments, a proximal end of the other catheter may be secured within the catheter adapter.

In some embodiments, a catheter system may include the delivery device and/or the catheter assembly. In some embodiments, the catheter assembly may be coupled to the distal end of the housing. In some embodiments, the first end of the instrument may be advanced in the distal direction beyond the distal end of the housing in response to the guide feature being partially and/or fully advanced along the slot in the distal direction.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1A is a top view of an example delivery device, illustrating an example catheter and example guidewire each in a fully retracted position, according to some embodiments;

FIG. 1B is a side view of the delivery device of FIG. 1A, illustrating the catheter and the guidewire each in the fully retracted position, according to some embodiments;

FIG. 1C is a cross-sectional view of the delivery device along line 1C-1C of FIG. 1B, according to some embodiments;

FIG. 1D is a cross-sectional view of the delivery device along line 1D-1D of FIG. 1B, according to some embodiments;

FIG. 2A is a top view of the delivery device of FIG. 1A, illustrating the catheter and the guidewire each in a fully advanced position, according to some embodiments;

FIG. 2B is a side view of the delivery device of FIG. 1A, illustrating the catheter and the guidewire each in the fully advanced position, according to some embodiments;

FIG. 2C is a cross-sectional view of the delivery device along line 2C-2C of FIG. 2B, according to some embodiments;

DESCRIPTION OF EMBODIMENTS

Figure 3A:
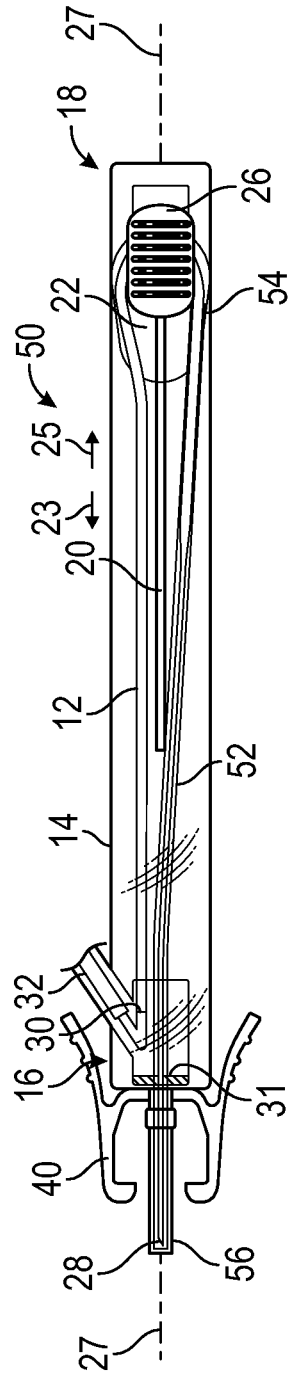
FIG. 3A is a top view of another example delivery device, illustrating an example instrument in a fully retracted position and example support tubing, according to some embodiments; p

Referring now to FIGS. 1A-1D, a delivery device 10 is illustrated, according to some embodiments. In some embodiments, the delivery device 10 may facilitate delivery of an instrument, such as, for example, a catheter 12, into an intravenous catheter assembly and/or a vein of a patient. In some embodiments, the delivery device 10 may facilitate placement of the catheter 12 into a second catheter, which may include an indwelling peripheral intravenous catheter ("PIVC"). In some embodiments, the instrument may include a probe (which may include a sensor), a light tube for disinfection, or another suitable instrument, which may be placed into the second catheter via the delivery device 10.

In some embodiments, the delivery device 10 may include a housing 14. In some embodiments, the housing may include a distal end 16, a proximal end 18, and a slot 20. In some embodiments, the housing 14 may encase or enclose the instrument when the instrument is in a retracted position. In some embodiments, the housing 14 may be cylindrical. In some embodiments, the housing 14 may be non-transparent. In some embodiments, as illustrated in FIGS. 1-4, the housing 14 may be transparent. In some embodiments, the instrument may be supported within the housing at one or more locations.

In some embodiments, the delivery device 10 may include a guide feature 22, which may be disposed within the housing 14. In some embodiments, the guide feature 22 may extend through the slot 20. In some embodiments, the guide feature 22 may include an advancement tab 26, which may be configured to be moved by a hand of a user. In some embodiments, the guide feature 22 may be moveable along the slot 20 to advance the instrument in a distal direction 23 and/or retract the instrument in a proximal direction 25.

In some embodiments, the advancement tab 26 may include various shapes, sizes, and configurations. In some embodiments, the advancement tab 26 may be disposed on a top, side, or bottom of the delivery device 10. In some embodiments, the slot 20 may be disposed in any portion of the housing 14. In some embodiments, the slot 20 may be disposed in a left or right side of the housing 14. In some embodiments, the slot 20 may be disposed in a top or bottom of the housing 14. In some embodiments, the slot 20 may be aligned with a longitudinal axis 27 of the delivery device 10. In some embodiments, the housing 14 may include multiple slots 20, which may allow for a particular guide feature 22 with an increased width to extend through the slots 20.

Figure 5A:
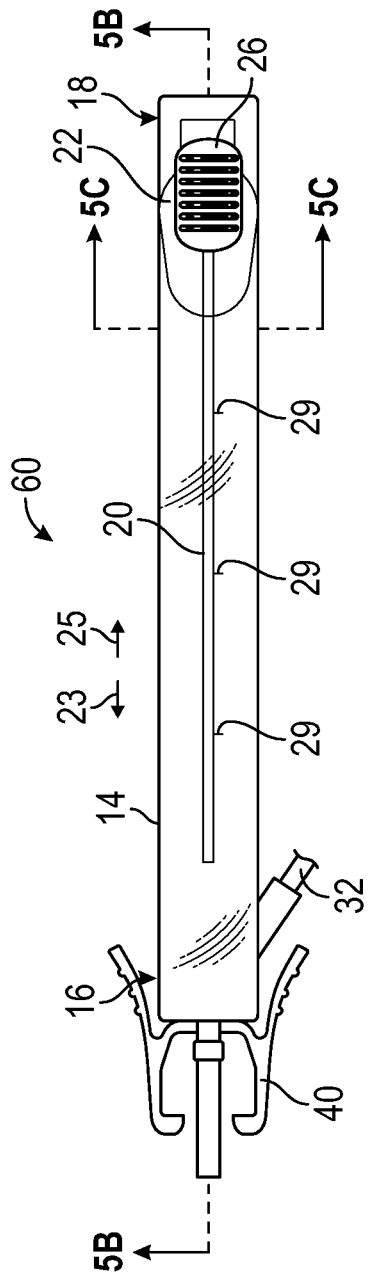
FIG. 5A is a top view of another example delivery device, illustrating the instrument in a fully retracted position, according to some embodiments.
Figure 5B:
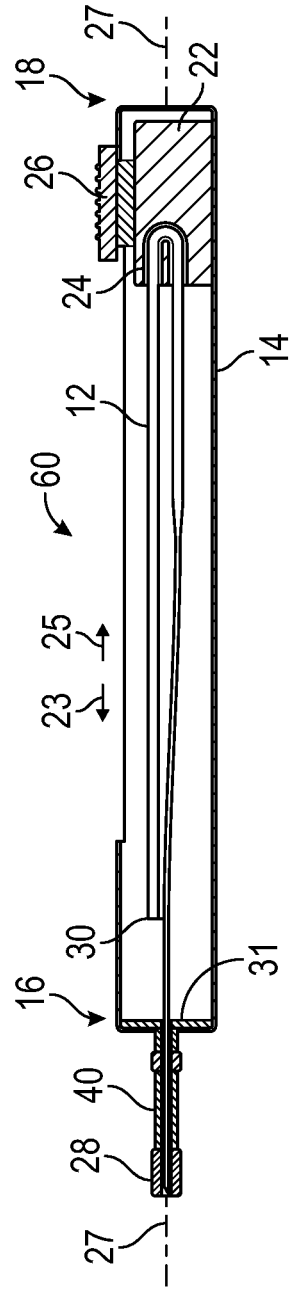
FIG. 5B is a cross-sectional view of the delivery device along line 5B-5B of FIG. 5A, illustrating the instrument in the fully retracted position, according to some embodiments.

In some embodiments, the guide feature 22 may include an instrument support structure, such as, for example, a channel 24. In some embodiments, the channel 24 may be generally U-shaped. In some embodiments, the channel 24 may include a U-shape having arms that are generally parallel to each other (as illustrated in FIG. 5B, for example). In some embodiments, the channel 24 may include a U-shape having arms that point away from or towards each other. In some embodiments, the support structure may include various shapes and configurations. In some embodiments, the channel 24 may be part of a tunnel, which may enclose the instrument. In some embodiments, the instrument may be disposed within the housing 14 and may extend through the guide feature 22. For example, in some embodiments, the instrument may extend through the channel 24.

In some embodiments, in response to movement of the guide feature 22 along the slot 20 in the distal direction 23, a first end 28 of the instrument may be advanced distally. In some embodiments, a second end 30 of the instrument may be stationary with respect to the housing 14. For example, in some embodiments, the second end 30 of the instrument may be fixed inside and/or to the housing 14.

In some embodiments, the delivery device 10 may include a blood control septum 31, which may be disposed within a lumen of the delivery device 10. In some embodiments, the septum 31 may be disposed proximate or towards the distal end 16 of the housing 14 of the delivery device 10. In some embodiments, the instrument may penetrate the septum 31 when the instrument is fully retracted or the instrument may penetrate the septum 31 in response to being advanced. In some embodiments, the septum 31 may prevent blood from entering an interior of the delivery device 10.

In some embodiments, the instrument may include the catheter 12, and the second end 30 of the instrument may be coupled to extension tubing 32. In some embodiments, the extension tubing 32 may be coupled to a blood collection device. In some embodiments, the blood collection device may include any suitable type of blood collection device. In some embodiments, the blood collection device may include a reservoir. In some embodiments, the blood collection device may include a vacuum tube, test tube, or syringe. In some embodiments, the blood collection device may include an adapter, which may be configured to hold a test tube or syringe. In some embodiments, a fluid pathway of the delivery device 10 may include the catheter 12 and the extension tubing 32.

In some embodiments, the catheter 12 may be used for fluid infusion and/or blood withdrawal. In some embodiments, a guidewire 34 may be disposed within the catheter 12. In some embodiments, the guidewire 34 may be used to facilitate placement of the catheter 12 within the vein of the patient, which may result in less vein-related trauma and may support the catheter 12 during advancement to prevent collapse or buckling of the catheter 12 as it advances through a second catheter (such as, for example, the catheter 65, illustrated in FIG. 6). It is understood that in some embodiments, the delivery device 10 may not include the guidewire 34.

In some embodiments, the guidewire 34 may include a first end 36 and a second end 38. In some embodiments, the guidewire 34 and the catheter 12 may be advanced and/or retracted together. In some embodiments, the second end 38 of the guidewire 34 may be stationary with respect to the housing. For example, in some embodiments, the second end 38 of the guidewire may be fixed inside the catheter 12 and/or the housing 14.

In some embodiments, the catheter 12 may include a multi-diameter catheter, such as described, for example, in U.S. Patent Application No. 62/660,646, filed Apr. 20, 2018, entitled "MULTI-DIAMETER CATHETER AND RELATED DEVICES AND METHODS," which is incorporated herein by reference. In some embodiments, the multi-diameter catheter may allow improved blood flow rates during blood collection. In some embodiments, an outer diameter of the guidewire 34 may be less than an inner diameter of the catheter 12 such that blood may flow around the guidewire 34 during blood collection.

FIGS. 1A-1C illustrate the catheter 12 and the guidewire 34 in a fully retracted position, prior to advancing the catheter 12 and the guidewire 34 or after returning the catheter 12 and the guidewire 34 from an advanced position, according to some embodiments. In some embodiments, when the guide feature 22 is fully retracted proximally to retract the catheter 12 and/or the guidewire 34, the guide feature 22 may contact a proximal end of the slot 20 and/or a proximal end 18 of the housing, which may act as a stop.

In some embodiments, the delivery device 10 may include a connector 40, which may be disposed at the distal end 16 of the housing 14. In some embodiments, the connector 40 may be configured to couple the delivery device 10 to the intravenous catheter assembly (as illustrated, for example, in FIG. 6). In some embodiments, the connector 40 may include a luer adapter, such as a slip or thread male or female luer adapter, or another suitable connector.

Figure 6:
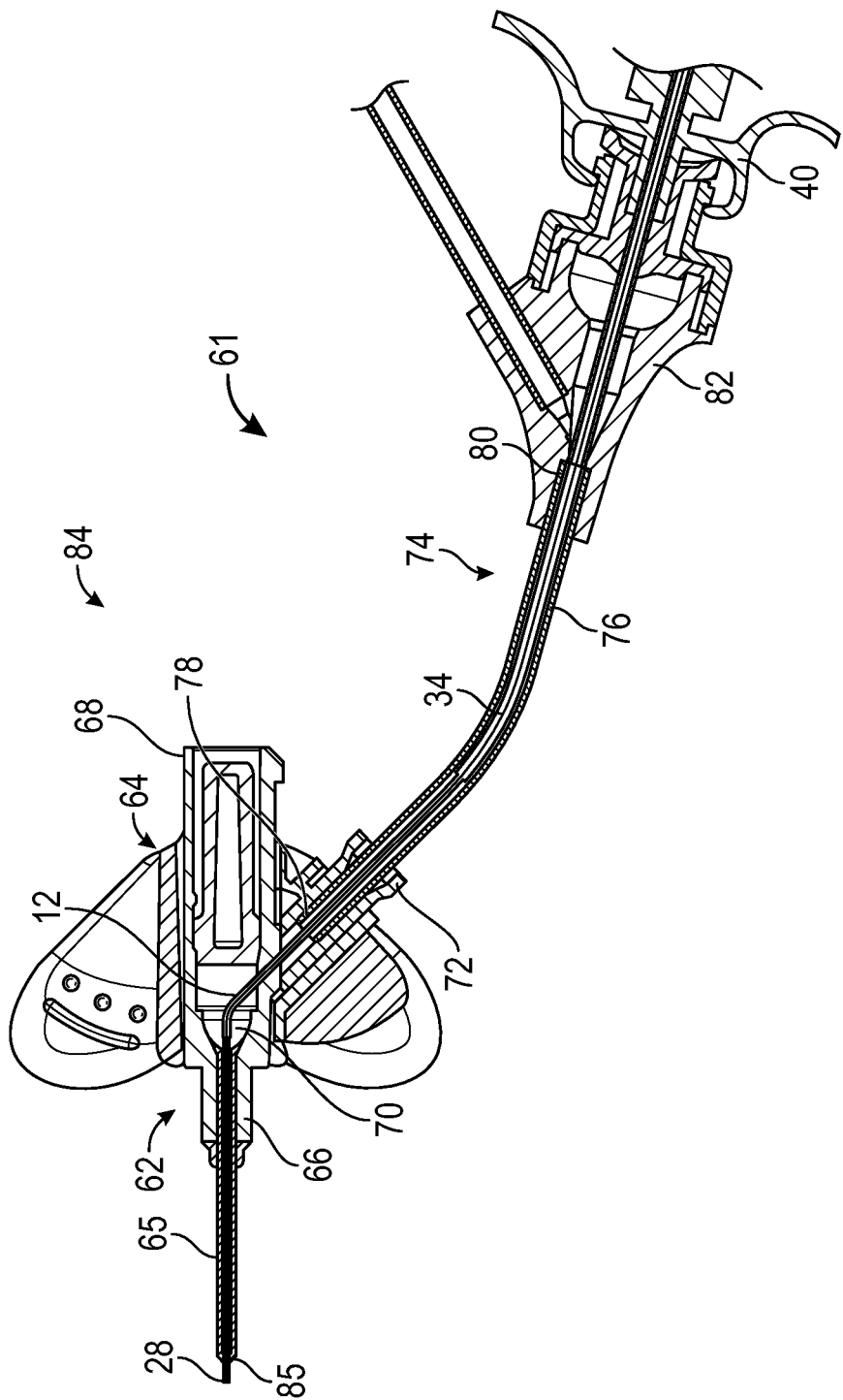
FIG. 6 is a cross-sectional view of an example catheter system, according to some embodiments.

In some embodiments, the channel 24 may be horizontally oriented within the housing, as illustrated in FIGS. 1-4. For example, arms of the channel 24 that is generally U-shaped may be positioned generally side by side when the delivery device 10 is coupled to a catheter assembly positioned for insertion into the patient, as illustrated in FIG. 6. In some embodiments, a portion of the instrument between the second end 30 of the instrument and the guide feature 22 may be generally parallel with the longitudinal axis 27, as illustrated, for example in FIGS. 1A and 1C. In some embodiments, the portion of the instrument between the second end 30 of the instrument and the guide feature 22 may be angled with respect to the longitudinal axis 27. In some embodiments, a portion of the instrument between the first end 28 of the instrument and the guide feature 22 may be parallel with respect to the longitudinal axis 27. In some embodiments, the portion of the instrument between the first end 28 of the instrument and the guide feature 22 may be angled with respect to the longitudinal axis 27, as illustrated, for example, in FIGS. 1A and 1C.

In some embodiments, the delivery device 10 may include one or more markings 29, which may provide a visual and/or tactile indication to the user of a position of the instrument. In further detail, in some embodiments, the markings 29 may indicate a distance that the instrument is advanced and/or retracted. For example, a particular marking 29 may correspond to a position of the guide feature 22 to position the distal end of the instrument at or near a tip of the catheter 12 or another location. In some embodiments, the markings 29 may be disposed on an outer surface of the delivery device 10. In some embodiments, at least some of the markings 29 may include detents and/or protrusions. In some embodiments, at least some of the markings 29 may include detents, which may be configured to hold the guide feature 22 at pre-determined positions and/or provide resistance to movement of the guide feature 22 from the detents.

Referring now to FIGS. 2A-2C, the guide feature 22 may be fully advanced, according to some embodiments. In some embodiments, when the guide feature 22 is fully advanced in the distal direction 23 to fully advance the instrument and/or the guidewire 34, the guide feature 22 may contact a distal end of the slot 20 and/or an inner surface of the housing 14, which may act as a stop.

In some embodiments, the first end 28 of the instrument may be advanced in the distal direction 23 beyond the distal end of the housing 14 in response to the guide feature 22 being partially and/or fully advanced along the slot 20 in the distal direction 23. In some embodiments, in response to movement of the guide feature 22 along the slot 20 in the distal direction 23 a first distance, the first end 28 of the instrument may be advanced in the distal direction 23 a second distance greater than the first distance. In some embodiments, the second distance may be two times the first distance ("a 1:2 advancement ratio").

If a particular guide feature were to be moved along a particular slot in the distal direction 23 the first distance, and a first end of a particular instrument advanced in the distal direction 23 a distance equal to the first distance (a "1:1 advancement ratio"), a length of a particular delivery device may need to be increased proportionally with a length of the instrument. Particularly when the instrument is long to provide a distant reach, this means the particular delivery device may also be long, which can significantly impact its use-ability, cost, and performance. As the length of the particular delivery device is increased, the instrument may be more likely to kink or collapse during advancement. In some embodiments, the 1:2 advancement ratio (or another advancement ratio where the second distance is greater than the first distance) between the guide feature 22 and the first end 28 of the instrument may provide reliability and structural support as the instrument is advanced, while also providing an instrument with long reach.

In some embodiments, the 1:2 advancement ratio (or another advancement ratio where the second distance is greater than the first distance) between the guide feature 22 and the first end 28 of the instrument may be accomplished by creating a U-shape in the instrument inside the housing 14 and supporting the instrument within the guide feature 22. Thus, in some embodiments, the delivery device 10 may facilitate support and advancement of an instrument having an increased length. In particular, in some embodiments, the channel 24 or another suitable structure of the guide feature 22 may support the instrument as the instrument is advanced through the channel 24 and distally into the vasculature. In some embodiments, the 1:2 advancement ratio between the guide feature 22 and the first end 28 of the instrument may include an approximately 1:2 advancement ratio between the guide feature 22 and the first end 28. In some embodiments, in response to movement of the guide feature 22 along the slot 20 in the distal direction 23 the first distance, the first end 28 of the instrument may be advanced in the distal direction 23 a second distance that is more than two times the first distance, which may include at least two times the first distance. In these and other embodiments, the instrument may be configured in multiple U-shapes and/or the delivery device 10 may include multiple U-shaped channels or other suitable support structures.

In some embodiments, in response to movement of the guide feature 22 along the slot 20 in the distal direction 23, the guidewire 34 may move through the channel 24 with the catheter 12. In some embodiments, the first end 36 of the guidewire 34 may be advanced in the distal direction 23 beyond the distal end of the housing 14 in response to the guide feature 22 being partially and/or fully advanced along the slot 20 in the distal direction 23.

In some embodiments, the first end 36 of the guidewire 34 may be disposed proximal and/or proximate to a transition in an inner diameter of the catheter 12 to allow blood or other fluid to flow in an annular space between an inner diameter of the catheter 12 and an outer diameter of the guidewire 34. In some embodiments, the guidewire 34 may provide support to the catheter 12 along a full or partial length of the catheter 12. In some embodiments, the guidewire 34 may improve structural reliability of the catheter 12, provide adequate blood collection fill time performance, reduce blood hemolysis risks or maintain adequate blood hemolysis risks, and reduce a risk of kinking of the catheter 12. In some embodiments, the housing 14 may facilitate full enclosure of the guidewire 34 and/or the catheter 12 upon completion of blood sampling.

Figure 3B:
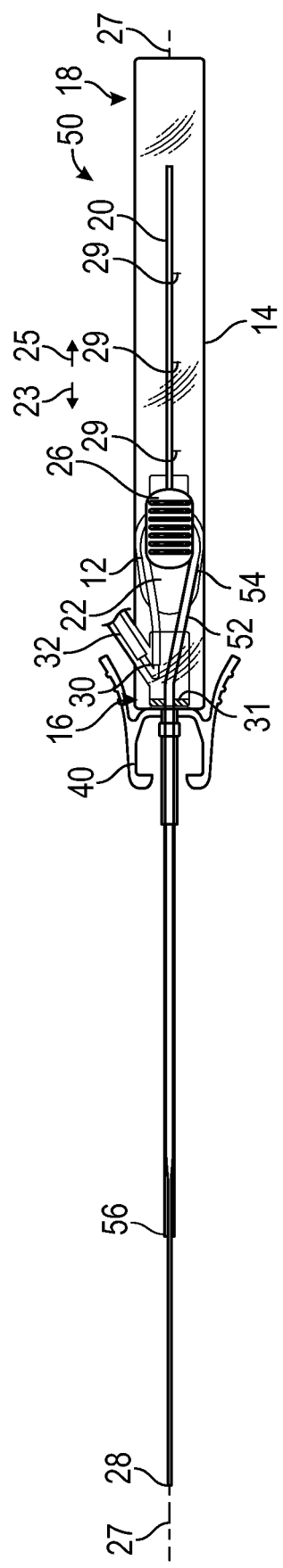
FIG. 3B is a top view of the delivery device of FIG. 3A, illustrating the instrument in a fully advanced position, according to some embodiments.

Referring now to FIGS. 3A-3B, in some embodiments, a delivery device 50 may include support tubing 52, which may extend from the guide feature 22. In some embodiments, a proximal end 54 of the support tubing 52 may be fixed to the guide feature 22. In some embodiments, the delivery device 50 may include or correspond to the delivery device 10 discussed with respect to FIGS. 1-2. In further detail, in some embodiments, the delivery device 50 may include one or more features of the delivery device 10. Similarly, in some embodiments, the delivery device 10 may include one or more features of the delivery device 50.

In some embodiments, in response to movement of the guide feature 22 along the slot 20 in the distal direction 23, the instrument may move through the support tubing 52. In some embodiments, the support tubing 52 may include a larger inner diameter than an outer diameter of the instrument such that the instrument may move through the support tubing 52. In some embodiments, the support tubing 52 may provide support to the first end 28 or the free end of the instrument. In some embodiments, in response to movement of the guide feature 22 along the slot 20 in the distal direction 23 the first distance, a distal end 56 of the support tubing 52 may be advanced in the distal direction 23 a distance equal to the first distance (a "1:1 advancement ratio"), while the first end 28 of the instrument may be advanced a distance greater than that of the first distance, such as for example, twice the first distance ("a 1:2 advancement ratio"). In some embodiments, the differing advancement ratios of the guide feature 22 with respect to the first end 28 and guide feature 22 with respect to the support tubing 52 may result in the support tubing 52 not advancing distally beyond a decreased diameter portion of the instrument, and the decreased diameter portion of the instrument advancing distally through the catheter assembly and into the vasculature.

Figure 4A:
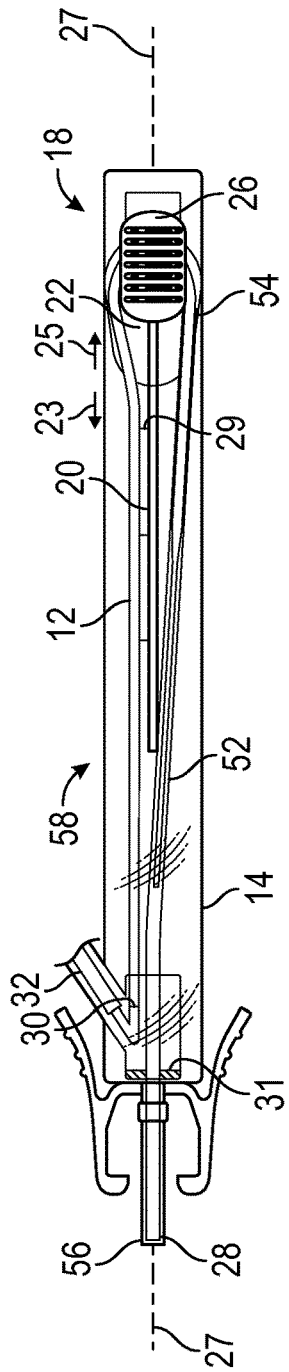
FIG. 4A is a top view of another example delivery device, illustrating an example instrument in a fully retracted position and example support tubing, according to some embodiments.
Figure 4B:
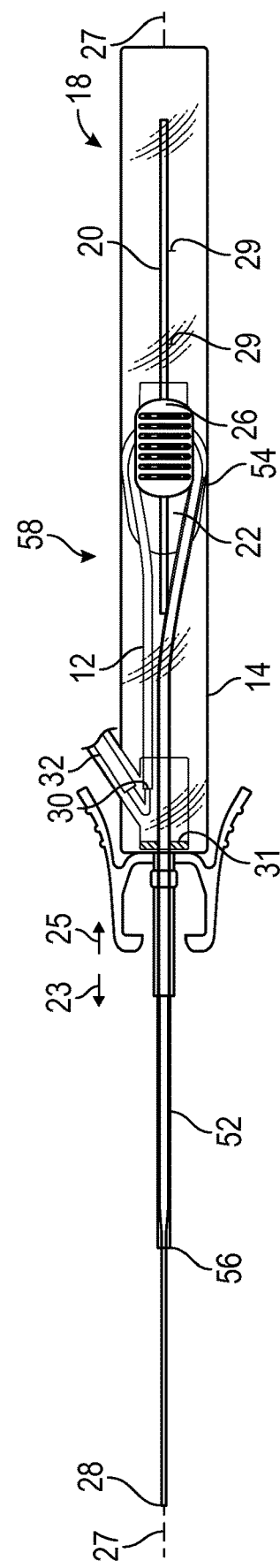
FIG. 4B is a top view of the delivery device of FIG. 3A, illustrating the instrument in a partially advanced position, according to some embodiments.
Figure 4C:
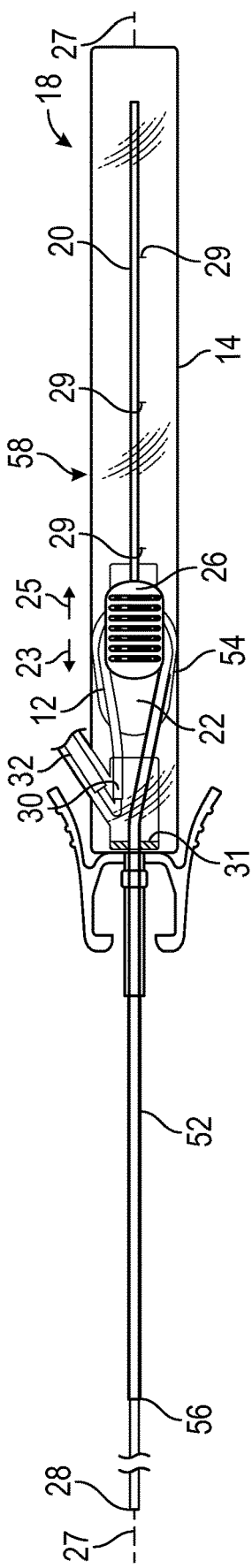
FIG. 4C is a top view of the delivery device of FIG. 3A, illustrating the instrument in a fully advanced position, according to some embodiments.

Referring now to FIGS. 4A-4C, in some embodiments, a delivery device 58 may facilitate a timed or delayed exit of the instrument from the support tubing 52. In further detail, in some embodiments, the first end 28 of the instrument may be shortened so that it is positioned proximal to at least a portion of the support tubing 52 when the guide feature 22 is fully retracted, as illustrated in FIG. 4A. In some embodiments, the delivery device 58 may include or correspond to the delivery device 10 and/or the delivery device 50 discussed with respect to FIGS. 1-3. In further detail, in some embodiments, the delivery device 58 may include one or more features of the delivery device 10 and/or the delivery device 50. Similarly, in some embodiments, the delivery device 10 and/or the delivery device 50 may include one or more features of the delivery device 58.

In some embodiments, given the 1:2 advancement ratio (or another advancement ratio where the second distance is greater than the first distance) between the guide feature 22 and the first end 28 of the instrument and the 1:1 advancement ratio between the guide feature 22 and the distal end 56 of the support tubing 52, the first end 28 of the instrument may exit the distal end 56 of the support tubing 52. In some embodiments, the first end 28 of the instrument may exit the distal end 56 of the support tubing 52 to facilitate entry of the instrument into a portion of the catheter assembly that may be too narrow for the support tubing 52 to enter.

In some embodiments, when the delivery device 50 includes the support tubing 52, the catheter 12 may be constructed of a softer material than polyimide, which may be less damaging to the vein wall. In these and other embodiments, the catheter 12 may include a tube constructed of one or more of polyurethane, silicon, thermoplastic elastomer ("TPE"), thermoplastic polyurethane ("TPU"), and another suitable compliant material.

Figure 5C:
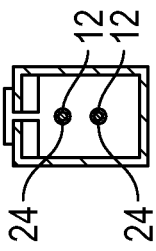
FIG. 5C is a cross-sectional view of the delivery device along line 5C-5C of FIG. 5A, according to some embodiments.

In some embodiments, the channel 24 may be disposed in various orientations within the housing 14. Referring now to FIGS. 5A-5C, in some embodiments, the channel 24 of a delivery device 60 may be vertically oriented within the housing 14. For example, arms of the channel 24 that is generally U-shaped may be positioned generally above and below each other when the delivery device 10 is coupled to a catheter assembly positioned for insertion into the patient, as illustrated in FIG. 6. In these embodiments, the first end 28 of the instrument may be disposed below the longitudinal axis 27, and the second end 30 of the instrument may be disposed above the longitudinal axis 27. Alternatively, in some embodiments, the first end 28 may be disposed above the longitudinal axis 27 and the second end 30 may be disposed below the longitudinal axis 27.

In some embodiments, the delivery device 60 may include or correspond to the one or more of the following: the delivery device 10, the delivery device 50, and the delivery device 58. In further detail, in some embodiments, the delivery device 60 may include one or more features of the delivery device 10, the delivery device 50, and/or the delivery device 58. Similarly, in some embodiments, the delivery device 10, the delivery device 50, and/or the delivery device 58 may include one or more features of the delivery device 60.

In some embodiments, a curvature of the U-shape may vary depending on, for example, on a bend radius of a material from which the instrument 24 is constructed. In some embodiments, the curvature of the U-shape may be configured to prevent kinking of or damage to the instrument 24.

Referring now to FIG. 6, in some embodiments, a catheter system 61 may include a catheter assembly 62 and/or a delivery device 84. In some embodiments, the delivery device 84 may include or correspond to the one or more of the following: the delivery device 10, the delivery device 50, the delivery device 58, and the delivery device 60. In further detail, in some embodiments, the delivery device 84 may include one or more features of the delivery device 10, the delivery device 50, the delivery device 58, and/or the delivery device 60. Similarly, in some embodiments, the delivery device 10, the delivery device 50, the delivery device 58, and/or the delivery device 60 may include one or more features of the delivery device 84.

In some embodiments, the delivery device 84 may be coupled to the catheter assembly 62, which may include a catheter adapter 64 and a catheter 65. In some embodiments, the catheter 65 may be indwelling. In some embodiments, the catheter 65 may include a PIVC. In some embodiments, the catheter 65 may be secured to the catheter adapter 64 and may extend distally from the catheter adapter 64. In some embodiments, the catheter adapter 64 may include a distal end 66, a proximal end 68, and a lumen 70 extending between the distal end 66 and the proximal end 68. In some embodiments, the distal end 66 and the proximal end 68 of the catheter adapter 64 may be axially aligned.

In some embodiments, the catheter system 61 may include a straight or non-integrated catheter adapter 64. In some embodiments, the catheter system 61 may include an integrated catheter adapter 64, as illustrated, for example, in FIG. 6. In further detail, in some embodiments, the IV catheter system may include a catheter adapter 64 having an integrated extension tube, such as, for example, the BD NEXIVA™ Closed IV Catheter System, the BD NEXIVA™ DIFFUSICS™ Closed IV Catheter System, or the Becton Dickinson PEGASUS™ Safety Closed IV Catheter System. In some embodiments, the catheter adapter 64 may include a side port 72 from which an extension tube 76 may extend.

In some embodiments, the catheter assembly 62 may include an extension set 74, which may be coupled to the catheter adapter 64. In some embodiments, the extension set 74 may include the extension tube 76, which may include a distal end 78 and a proximal end 80. In some embodiments, the extension tubing 76 may extend from the side port 72.

In some embodiments, the catheter assembly 62 may include a connector 82, which may be configured to couple the delivery device 84 to the catheter assembly 62. In some embodiments, the connector 82 may be coupled to the proximal end 80 of the extension tubing 76. In other embodiments, the connector 82 may be disposed at the proximal end 68 of the catheter adapter 64 or another location. In some embodiments, the connector 82 may include a luer adapter, such as a male or female luer adapter, or another suitable connector.

In some embodiments, the first end 36 of the guidewire 34 and/or the first end 28 of the instrument may be disposed distal to the distal end of the catheter 65 when the instrument and the guidewire 34 are fully and/or partially advanced. In some embodiments, the catheter 12 may provide structural support to the catheter 65. In some embodiments, the catheter 12 may allow the user to draw a blood sample or infuse fluid through the catheter 65 when the catheter 65 is no longer functional or safe due to, for example, debris build up on a tip 85 of the catheter 65 and/or collapse of the catheter 65. Thus, in some embodiments, the catheter 12 may reduce a number of needle sticks that the patient experiences as the catheter 65 may be replaced less frequently.

In some embodiments, delivery of the catheter 12 into the catheter system 61 and/or the vasculature of the patient may reduce blood hemolysis and a risk of kinking of the catheter 65. In some embodiments, the delivery device 84 may allow use of the guidewire 34, which may improve placement of the catheter 12 within the vasculature. In some embodiments, the connector 82 may be disposed remotely from the patient, which may reduce a risk of disturbing an insertion site of the catheter 65.

It is understood that in some embodiments, the catheter 12 and/or the guidewire 36 may be replaced with another instrument, such as, for example, a probe (which may include a sensor), a light tube for disinfection, or another suitable instrument.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A delivery device for delivering a catheter into a catheter assembly, the delivery device comprising:
   a housing having a proximal end, a distal end, and a slot;
   a guide feature disposed within the housing, wherein the guide feature extends through the slot, wherein the guide feature comprises a channel, wherein the channel is generally U-shaped;
   a catheter disposed within the housing and extending through the channel that is generally U-shaped, wherein in response to movement of the guide feature along the slot in a distal direction, the catheter moves through the channel and a first end of the catheter is advanced in the distal direction, wherein a second end of the catheter is stationary with respect to the housing; and
   a guidewire disposed within the catheter, wherein in response to movement of the guide feature along the slot in the distal direction, the guidewire and the catheter move together through the channel.

2. The delivery device of claim 1, wherein in response to movement of the guide feature along the slot in the distal direction a first distance, the first end of the catheter is advanced in the distal direction a second distance, wherein the second distance is greater than the first distance.

3. The delivery device of claim 1, wherein the first end of the catheter is advanced in the distal direction beyond the distal end of the housing in response to the guide feature being fully advanced along the slot in the distal direction.

4. The delivery device of claim 1, wherein the housing further comprises extension tubing extending outwardly from a distal portion of the housing, wherein the second end of the catheter is coupled to the extension tubing.

5. The delivery device of claim 1, wherein a first end of the guidewire is advanced in the distal direction beyond the distal end of the housing in response to the guide feature being fully advanced along the slot in the distal direction.

6. The delivery device of claim 1, wherein in response to movement of the guide feature along the slot in the distal direction a first distance, a first end of the guidewire is advanced in the distal direction a second distance, wherein the second distance is greater than the first distance.

7. The delivery device of claim 1, further comprising support tubing extending from the guide feature and coupled to the guide feature, wherein in response to movement of the guide feature along the slot in the distal direction a first distance, the catheter moves through the support tubing and a first end of the support tubing is advanced in the distal direction the first distance.

8. The delivery device of claim 1, wherein the channel is horizontally oriented within the housing.

9. The delivery device of claim 1, wherein the channel is vertically oriented within the housing.

10. The delivery device of claim 1, wherein a portion of the catheter between the second end of the catheter and the guide feature is generally parallel with a longitudinal axis of the delivery device.

11. The delivery device of claim 1, wherein a portion of the catheter between the second end of the catheter and the guide feature is angled with respect to a longitudinal axis of the delivery device.

12. The delivery device of claim 1, wherein a portion of the catheter between the first end of the catheter and the guide feature is parallel with a longitudinal axis of the delivery device.

13. The delivery device of claim 1, wherein a portion of the catheter between the first end of the catheter and the guide feature is angled with respect to a longitudinal axis of the delivery device.

14. The delivery device of claim 1, wherein the guide feature further comprises an advancement tab configured to be moved by a hand of a user.

15. A delivery device for delivering a catheter into a catheter assembly, the delivery device comprising:
   a housing having a proximal end, a distal end, and a slot;
   a guide feature disposed within the housing, wherein the guide feature extends through the slot, wherein the guide feature comprises a channel, wherein the channel is generally U-shaped;
   a catheter disposed within the housing and extending through the channel that is generally U-shaped, wherein in response to movement of the guide feature along the slot in a distal direction, the catheter moves through the channel and a first end of the catheter is advanced in the distal direction, wherein a second end of the catheter is stationary with respect to the housing; and
   a guidewire disposed within the catheter and the channel that is generally U-shaped, wherein the guidewire is spaced apart from the catheter such that blood flows between the guidewire and the catheter and through the channel; and wherein in response to movement of the guide feature along the slot in the distal direction, the guidewire and the catheter move together through the channel.

* * * * *